(12) United States Patent
Niwa et al.

(10) Patent No.: US 7,432,073 B2
(45) Date of Patent: Oct. 7, 2008

(54) METHOD FOR DETECTING GUAIACOL PRODUCING BACTERIA

(75) Inventors: Motohiro Niwa, Fujisawa (JP); Atsuko Kawamoto, Samukawa-Machi (JP); Akemi Kuriyama, Samukawa-Machi (JP)

(73) Assignee: Kirin Beverage Corporation, Tokyo (JP)

( * ) Notice: Subject to any disclaimer, the term of this patent is extended or adjusted under 35 U.S.C. 154(b) by 582 days.

(21) Appl. No.: 10/487,085

(22) PCT Filed: Apr. 28, 2003

(86) PCT No.: PCT/JP03/05460

§ 371 (c)(1),
(2), (4) Date: Feb. 19, 2004

(87) PCT Pub. No.: WO2004/040007

PCT Pub. Date: May 13, 2004

(65) Prior Publication Data

US 2005/0272115 A1    Dec. 8, 2005

(30) Foreign Application Priority Data

Oct. 31, 2002  (JP)  ............................. 2002-317851
Feb. 24, 2003  (JP)  ............................. 2003-046327

(51) Int. Cl.
*C12Q 1/04*  (2006.01)
(52) U.S. Cl. .............................. 435/34; 435/41; 435/28
(58) Field of Classification Search ................... 435/34, 435/41, 28
See application file for complete search history.

(56) References Cited

U.S. PATENT DOCUMENTS 6,235,507 B1 * 5/2001 Muheim et al. ............. 435/147
2003/0129621 A1 * 7/2003 Takaichi et al. ................. 435/6

FOREIGN PATENT DOCUMENTS

JP         7-68 A      1/1995
JP      07-123998    *  5/1995

OTHER PUBLICATIONS

Crawford R. et al. Microbial Catabolism of Vanillate. Applied and Environmental Microbiology 36(4)539-543, Oct. 1978.*
Pettipher G. et al. Methods for the Detection and Enumeration of *A. acidoterrestris* and Investigation of Growth and Production of Taint in Fruit Juice and Fruit Juice Containing Drinks. Letters in Applied Microbiology vol. 24 185-189, 1997.*
JP 7-123998 A (Daiwa Can Co., Ltd.) May 16, 1995 & JP 3177367 B2.
Chow, K. T., et al., Characterization of a vanillic acid non-oxidative decarboxylation gene cluster from *Streptomyces* sp.D7. Microbiology 1999, vol. 145, pp. 2393-2403.
Crawford, R. L., Microbial catabolism of vanillate: decarboxylation to guaiacol. Appl. Environ. Microbiol. 1978, vol. 36, pp. 539-543.
WO 90/02817 A1 (Oriental Yeast Co., Ltd.) Mar. 22, 1990 & JP 63-214199 A.
Pettipher, G. L., et al., "Methods for the detection and enumeration of *Alicyclobacillus acidoterrestris* and investigation of growth and production of taint in fruit juice and fruit-juice containing drinks", Lett. Appl. Microbiol., vol. 24, pp. 185-189 (1997).
Orr, R. V., et al., Detection of guaiacol produced by *Alicyclobacillus acidoterrestris* in apple juice by sensory and chromatographic analyses, and comparison with spore and vegetative cell populations., J. Food Prot., vol. 63, pp. 1517-1522 (2000).
JP 10-234376 A (Kirin Beverage KK) Sep. 8, 1998 (Abst.).
JP 08-140696 A (Kirin Beverage KK) Jun. 4, 1996 (Abst.).
Jensen, N., et al., Formation of guaiacol in chocolate milk by the psychrotrophic bacterium *Rahnella aquatilis*, Lett. Appl. Microbiol., vol. 33, pp. 339-343 (2001).
Huang, Z., et al., "Mechanisms of ferulic acid conversions to vanillic acid and guaiacol by *Rhondotorula rubra*", J. Biol. Chem., vol. 268, pp. 23954-23958 (1993).
Japanese Office Action dated Apr. 7, 2006 for corresponding JP2003-046327.

(Continued)

*Primary Examiner*—Ralph Gitomer
(74) *Attorney, Agent, or Firm*—Darby & Darby P.C.

(57) ABSTRACT

The present invention relates to a method capable of detecting proliferative bacteria in food and beverage, particularly acid or neutral beverage at low cost within a short time, a detection kit which enables simple measurement, and a technology for examination of harmful bacteria in food and beverage with respect to a method for rapid determination of proliferation properties of bacteria capable of producing guaiacol in food and beverage.

There is disclosed a method for detecting bacteria capable of producing guaiacol, which comprises culturing or incubating a culture solution containing a specimen for a predetermined time in the presence of vanillic acid, and measuring the produced guaiacol by qualitative or quantitative analysis.

Also there is disclosed a kit for detection of bacteria capable of producing guaiacol, comprising a container, and an acid or neutral culture medium containing a vanillic acid substrate for production of guaiacol, which is contained in the container and also sterilized and sealed.

Furthermore there is disclosed a method for rapid determination of proliferation properties of bacteria capable of producing guaiacol in food and beverage, which comprises incubating a sporophyte of spore-forming bacteria capable of producing guaiacol for a predetermined time in the food and beverage in the presence of vanillic acid, and measuring the produced guaiacol by qualitative or quantitative analysis.

11 Claims, 3 Drawing Sheets

OTHER PUBLICATIONS

"Development of Method for Rapidly Detecting *A. acidoterrestris*, Harmful Bacteria in Beverage" by Matsubara et al., Research Presentation, Research and Development Laboratory of Kirin Beverage Corporation, Sep. 13, 2002, vol. 45, pp. 19-20 and its English translation, pp. 1-3.

"Microbial Catabolism of Vanillate: Decarboxylation to Guaiacol" by Crawford, et al., University of Minnesota, Freshwater Biological Institute and Department of Microbiology, Navarre, Minnesota, Applied and Environmental Microbiology, Oct. 1978, vol. 36, No. 4, pp. 539-543.

Patent Abstracts of Japan for JP7-68 published on Jan. 6, 1995.

* cited by examiner

METHOD FOR DETECTING GUAIACOL PRODUCING BACTERIA

CROSS-REFERENCE TO PRIOR APPLICATION

This is a National Phase Application under 35 U.S.C. §371 of International Patent Application No. PCT/JP2003/05460 filed Apr. 28, 2003, which claims the benefit of Japanese Patent Application No. 2003-46327 filed Feb. 24, 2003 and Japanese Patent Application No. 2002-317851, filed Oct. 31, 2002, both of which are incorporated by reference herein. The International Application was published in Japanese on May 13, 2004 as WO 2004/040007 A1 under PCT Article 21(2).

TECHNICAL FIELD

The present invention relates to an examination of harmful bacteria in foods and beverages and, specifically, to a detection and a rapid determination of proliferation properties thereof. More particularly, it relates to a method and a kit for detecting bacteria capable of producing guaiacol, particularly thermotolerant acidophilic bacteria (for example, *A. acidoterrestris*) which are harmful to acidic beverage, or bacteria belonging to the genus *Bacillus* (for example, *Bacillus subtilis*) and the like which is harmful to neutral beverage, and a method for rapid determination of proliferation properties.

BACKGROUND ART

Microorganisms having proliferation properties have recently been detected from acidic foods and beverages, particularly acidic beverage such as raw fruit juice and fruit juice, resulting in a problem. In general, bacteria hardly generate in an acid range like fruit juice and fruit juice beverage. However, thermotolerant acidophilic bacteria having thermotolerant spores among acidophilic bacteria which is fond of the acid range hardly die out under the conditions of a sterilization temperature of the beverage (usually about 93° C.), thus constituting a large problem. Typical thermotolerant acidophilic bacteria include bacteria of the genus *Alicyclobacillus*. It has been reported that two species (*A. acidoterrestris* and *A. acidiphilus*) among bacteria of the genus *Alicyclobacillus* contaminate fruit juice and fruit juice beverage to cause proliferation. Also these bacteria constitute a large problem on quality because a nasty smell component, guaiacol, is produced during proliferation. Particularly, *A. acidoterrestris* is isolated from fruit juice with high frequency and is considered as an indicator bacterium in control of microorganism of fruit juice and fruit juice-containing beverage.

As a method for detecting such bacteria, there have been developed, e.g., a culturing method and a method for detecting a specific gene by PCR, which are described in Patent Documents described hereinafter. However, the culturing method, which requires no expensive devise, require the culture or detection time of about 48 hours or more after pre-culture and a simple method for detection within a short time has never been known.

Japanese Patent No. 3177367 discloses a method for detecting acidophilic spore-forming bacteria using an acid culture medium containing aldehyde and a detection kit. It also discloses that, since acidophilic spore-forming bacteria converts vanillin into guaiacol and guaiacol emits a strong odor, the presence of acidophilic spore-forming bacteria in a test sample can be detected within a short time without confirming the formation of colony by adding a test sample such as fruit juice in a vanillin-containing medium.

Japanese Patent Laid-Open Publication No. 8-140696 discloses, in a method for detecting thermotolerant acidophilic bacteria having proliferation properties in acid fruit juice or acidic beverage, the presence of the bacteria can be evaluated by the presence or absence of ω-cyclohexane fatty acid using a GC-MS method and the like.

Japanese Patent Laid-Open Publication No. 10-234376 discloses a method for detecting thermotolerant acidophilic bacteria having proliferation properties in acid fruit juice or acidic beverage, which comprises detecting and identifying microorganisms belonging to the genus *Alicyclobacillus* by subjecting a nucleic acid coding for an enzyme involving in bio-synthesis of ω-cyclohexane fatty acid to the PCR reaction using a nucleic acid primer having a specific base sequence.

Although various dairy products with vanilla flavor are commercially available, the production of a nasty smell component, guaiacol, associated with proliferation of specific *Bacillus* may cause deterioration of flavor, if the conditions are satisfied. However, harmfulness of microorganisms belonging to the genus *Bacillus* has little been noticed, and thus a method for detecting harmful microorganisms has scarcely been reported.

The present inventors have hitherto carried out a challenge test (indicator bacteria proliferation test method) using *Alicyclobacillus acidoterrestris* as a means for understanding proliferation properties of bacteria in a specimen. In this test method, bactericidal conditions are determined by inoculating $10^{1-3}$/ml of spores (or vegetative cells) into a specimen such as beverage, standing at 35° C. for 2 to 3 weeks, measuring an increase or decrease of bacteria with a lapse of time using a plating culture method (requiring additional 3 to 5 days), and performing risk analysis due to the thermotolerant acidophilic bacteria in the beverage. Therefore, the determination requires at least a half-month.

DISCLOSURE OF THE INVENTION

In light of the above-mentioned problems of the prior art, an object of the present invention is to provide a method capable of detecting harmful bacteria such as thermotolerant acidophilic bacteria having proliferation properties in food and beverage, particularly acidic beverage such as acid juice (mainly *A. acidoterrestris* and *A. acidiphilus*, particularly *A. acidoterrertris*), bacteria belonging to the genus *Bacillus* having proliferation properties in neutral food and beverage, particularly dairy products (for example, yogurt) and neutral food and beverage such as tea (mainly, *B. subtilis* and *B. megaterium*, particularly *B. subtilis*) at low cost within a short time, an examination kit which enables simple measurement, and a rapid method for determination of proliferation properties of bacteria in the food and beverage on the basis of the harmful bacteria as indicators.

It is known that guaiacol is produced only by several *Bacillus* and *Actinomyces* (see, R. F. SIMPSON, J. M. AMON and A. J. DAW, Off-flavour in wine caused by guaiacol, Food Technology in Australia, vol. 38, 31-33 (1986), and N. Jensen, P. Varelis and F. B. Whitfield, Formation of guaiacol in chocolate milk by the psychrotrophic bacterium *Rhanella aguatilis*, Lettes in Applied Microbiology, 33, 339-343 (2001)). It is known that thermotolerant acidophilic bacterium *A. acidoterrestris* is one of these bacteria and contaminates acidic beverage, and also produces guaiacol from vanillin via vanillic acid. Based on such information, the present inventors made a trial of developing rapid and simple detection method and kit using a specific culturing method of bacteria capable of producing guaiacol, particularly thermotolerant acidophilic bacteria and bacteria belonging to the genus *Bacillus*.

As a result, the present inventors have achieved the above object by culturing a test sample in the presence of vanillic acid and measuring the produced guaiacol. Based on this finding, the present inventors have succeeded in the development of rapid and simple detection method and kit using a culturing method of bacteria capable of producing guaiacol, particularly thermotolerant acidophilic bacteria (particularly *A. acidoterrestris*) and bacterial of the genus *Bacillus* (particularly *B. subtilis*), which is more rapid and simple as compared with a conventional method, and a method for rapid determination of proliferation properties in food and beverage.

That is, the present invention provides the following detection methods (1) to (6), detection kits (7) to (13), and methods for rapid determination of proliferation properties (14) to (17).

(1) A method for detecting bacteria capable of producing guaiacol, which comprises culturing or incubating a culture solution containing a specimen for a predetermined time in the presence of vanillic acid, and measuring the produced guaiacol by qualitative or quantitative analysis.
(2) The method described in (1), wherein said produced guaiacol is measured by GC-MS analysis or color reaction.
(3) The method described in (1) or (2), wherein the color reaction for guaiacol employs an oxidation reaction using peroxidase as a catalyst and is detected by spectrophotometry or visual observation.
(4) The method described in any one of (1) to (3), wherein said bacteria capable of producing guaiacol to be detected are thermotolerant acidophilic bacteria and are cultured or incubated under an acid condition.
(5) The method described in any one of (1) to (3), wherein said bacteria capable of producing guaiacol to be detected are bacteria belonging to the genus *Bacillus* and are cultured or incubated under a neutral condition.
(6) The method described in (4), wherein said thermotolerant acidophilic bacteria are of *A. acidoterrestris*.
(7) A kit for detection of bacteria capable of producing guaiacol, comprising a container, and an acid or neutral culture medium containing a vanillic acid substrate for production of guaiacol, which is contained in the container and also sterilized and sealed.
(8) A kit for detection of bacteria capable of producing guaiacol, comprising a combination of the kit described in (7) and a means for detection of guaiacol in combination.
(9) The kit described in (7) or (8), wherein said means for detection of guaiacol is based on color reaction and includes a combination of at least hydrogen peroxide water, a peroxidase enzyme and a buffer for enzymatic reaction.
(10) The kit for detection of bacteria capable of producing guaiacol described in (9), comprising all or any combination of the kit described in (7), a vanillic acid substrate, hydrogen peroxide water, peroxidase, a buffer solution, a filter for filtrating a culture solution, a manual pump for filtrating a culture solution, a transparent cell containing a culture filtrate and a color sample plate.
(11) The kit described in any one of (7) to (10), wherein said bacteria capable of producing guaiacol to be detected are thermotolerant acidophilic bacteria and an acid culture medium is contained therein.
(12) The kit described in any one of (7) to (10), wherein said bacteria capable of producing guaiacol to be detected are bacteria belonging to the genus *Bacillus* and a neutral culture medium is contained therein.
(13) The kit described in (11), wherein said thermotolerant acidophilic bacteria are of *A. acidoterrestris*.
(14) A method for rapid determination of proliferation properties of bacteria capable of producing guaiacol in food and beverage, which comprises incubating a sporophyte of spore-forming bacteria capable of producing guaiacol for a predeterimined time in the food and beverage in the presence of vanillic acid, and measuring the produced guaiacol by qualitative or quantitative analysis.
(15) The method described in (14), wherein said bacteria capable of producing guaiacol to be measured are thermotolerant acidophilic bacteria.
(16) The method described in (15), wherein said thermotolerant acidophilic bacteria are of *A. acidoterrestris*.

BEST MODE FOR CARRYING OUT THE INVENTION

In the present invention, main subject includes acidic and neutral foods and beverages. Bacteria which contaminate acidic food and beverage, particularly acidic beverage such as fruit beverage to cause proliferation are generally bacteria of the genus *Alicylobacillus*. Typical bacteria of the genus *Alicyclobacillus* include the following seven species: *A. acidoterrestris, A. acidocaldarius, A. cycloheptanicus, A. hesperidum, A. herbarius, A. mali,* and *A. acidiphilus*. Among bacteria of the genus *Alicyclobacillus*, bacteria which are isolated from fruit juice with high frequency to produce a chemical-like nasty smell component, guaiacol, during proliferation are limited to the following tow species: *A. acidoterrestris* and *A. acidiphilus*. Among these bacteria, *A. acidoterrestris* is isolated from beverage and fruit juice with high frequency. Bacteria which contaminate neutral food and beverage, particularly neutral food and beverage such as dairy product and tea to cause proliferation are generally bacteria of the genus *Bacillus*. Therefore, an examination of the presence or absence of their harmful bacteria is important to control microorganism. Thus the present inventors have taken notice of the production process of guaiacol which can serve as one of indicators for harmful bacteria in acidic and neutral beverages and have found that guaiacol is produced from vanillin via vanillic acid. It is known that an enzyme, which catalyzes the production of guaiacol, is a decarboxylation reaction due to vanillic acid decarboxylase. The present inventors have made a comparison in rapidness of the detection of *A. acidot-*

*errestris* between the method of culturing a specimen by the addition of vanillin (method described in Japanese Patent No. 3177367) and the method of culturing a specimen by the addition of vanillic acid. As a result, it has been confirmed that, in case of the addition of vanillic acid, the guaiacol production rate is by far higher than that in case of vanillin, as shown in Examples described hereinafter. Also in case of various bacteria belonging to the genus *Bacillus*, results of remarkably high guaiacol production rate could be obtained. In the present invention, microorganisms as the subject are not specifically limited as far as they are bacteria capable of producing guaiacol.

As described above, the detection method of the present invention is a method for detecting bacteria capable of producing guaiacol, which comprises culturing or incubating a culture solution containing a specimen for a fixed time in the presence of vanillic acid, and measuring the produced guaiacol by qualitative or quantitative analysis. In a preferable embodiment, it is a method wherein the produced guaiacol is measured by GC-MS analysis or color reaction.

The term "specimen" in the present invention refers to a sample which may contain harmful bacteria and is to be detected by using the detection method and the detection kit of the present invention and examples thereof include, but are not limited to, raw fruit juice (acidic juice such as apple juice or orange juice), acidic juice such as fruit juice (for example, orange juice or fruit juice), neutral food and beverage such as dairy product (milk or yogurt (particularly semi-product) or the like), rice gruel, tea and mixed tea, and food and beverage including food such as isomerized sugar or honey, and bacterial cells obtained after culturing them. Examples of the bacterial cells obtained after culture include liquid culture or colony which was selectively cultured (pre-culture) using an acid liquid culture medium or a solid culture medium and a neutral liquid culture medium or a solid culture medium, and dilution thereof. Examples of the acid culture medium include liquid or solid culture medium used commonly as a selection medium for acidophilic bacteria (for example, YSG medium, or BAM medium), and acidic food and drink per se such as acidic beverage as a specimen. In case of pre-culturing a specimen such as acidic beverage, generally, the specimen is directly cultured at a temperature of 35 to 45° C. for about 1 to 5 days, or cultured at a temperature of 45 to 50° C. for about 48 to 96 hours using the liquid culture medium or solid culture medium. Example of the neutral culture medium include liquid or solid culture medium used commonly as a selection medium for detection of *Bacillus* (for example, standard agar medium or TSA medium), and neutral food and drink per se such as neutral beverage as a specimen. In case of pre-culturing a specimen such as a neutral beverage, generally, the specimen is cultured directly at a temperature of 30 to 35° C. for about 7 to 10 days, or cultured at a temperature of 30 to 35° C. for about 48 to 72 hours using the liquid culture medium or solid culture medium.

The term "culture solution" as used herein refers to a specimen-containing liquid medium (or culture medium) or culture medium-free liquid which can maintain cell viability, for example, sterilized water or buffer solution, which is a subject in culture or incubation in the presence of vanillic acid.

The detection method according to the present invention basically include the following cases: a case of culturing a specimen such as acidic beverage (or neutral beverage) in an acid medium (or neutral medium) containing vanillic acid added therein, or adding vanillic acid to a specimen such as acidic beverage (or neutral beverage) and culturing, thereby to simultaneously perform selective culture (pre-culture) and guaiacol production reaction; and a case of incubating pre-cultured (selectively cultured) culture such as bacterial cells after culture in a culture solution containing vanillic acid, or adding vanillic acid to the culture and incubating, thereby to perform the guaiacol production reaction. In case of adding vanillic acid to acidic beverage, neutral beverage, liquid culture or cultured fruit juice, these liquid samples (specimens) themselves serve as a culture solution in the present invention.

The culture as described above is basically carried out in the following form.

(1) A specimen such as acidic beverage (or neutral beverage) or solid food (e.g., retort Okowa (steamed rice with red beans)), semi-liquid food (for example, yogurt) is added to a liquid medium containing vanillic acid added therein and cultured selectively at a temperature of 45 to 50° C. for about 18 to 48 hours (pre-culture and guaiacol production reaction). Examples of the liquid medium include acid medium such as YSG medium and BAM medium; standard medium; and neutral medium such as TSB medium. The concentration of vanillic acid added is usually within a range from about 25 to 200 ppm, and preferably from about 50 to 100 ppm (medium containing vanillic acid added therein) based on the medium. The amount of the specimen added is usually within a range from 10 to 50% (v/v) based on the medium.

(2) Vanillic acid is added to a specimen such as acidic beverage (or neutral beverage) and cultured usually at a temperature of 35 to 45° C. for about 18 to 48 hours (pre-culture and guaiacol production reaction). The concentration of vanillic acid is usually within a range from about 25 to 200 ppm based on the specimen.

(3) A liquid culture or colony obtained previously by selective culturing (pre-culturing) is added directly to above-mentioned liquid medium containing vanillic acid added therein, or added after optionally diluting with sterilized water, proper buffer solution (for example, potassium phthalate buffer solution (for acid medium), potassium phosphate buffer solution (for neutral medium), liquid medium (for example, YSG medium (for acid medium), TSB medium (for neutral medium) or the like, and then cultured usually at a temperature of 45 to 50° C. (particularly for thermotolerant acidophilic bacteria) or 35 to 45° C. (particularly for bacteria of the genus *Bacillus*) for about 1 to 8 hours, and preferably about 1 to 3 hours with shaking (guaiacol production reaction). The amount of the specimen is, for example, one scrape of a platinum loop (per 5 to 10 ml of the medium) or about 1 to 10% (v/v) of the liquid culture or dilution based on the medium.

(4) Vanillic acid is added to a liquid culture obtained previously by selective culturing (pre-culturing) or the dilution of the culture or colony, and then cultured usually at a temperature of 45 to 50° C. for about 0.5 to 1.5 hours with shaking (guaiacol production reaction). The amount of vanillic acid is usually from about 25 to 200 ppm, and preferably from about 50 to 100 ppm, based on above-mentioned liquid culture or dilution.

In case of using a liquid culture or colony as a specimen, the concentration of the bacterial cells in a culture solution containing vanillic acid added therein is usually controlled within a range from about $10^5$ to $10^7$/ml, and preferably from about $10^5$ to $10^6$/ml.

In case of the above cases (2) and (4), vanillic acid to be added may be in the form of being dissolved in the above liquid medium or the other proper medium, or may be in the form of being dissolved in a medium-free liquid such as ethanol or water.

The culture according to the above cases (1) to (4) is usually carried out under the conditions of the pH within a range from about 3.0 to 5.0 (for acid medium), or from about 5.5 to 7.5 (for neutral medium).

The pre-culture (selective culture) and the guaiacol production reaction simultaneously proceed in the above cases (1) and (2), while the guaiacol production reaction is carried out after the selective culture (pre-culture) in the above cases (3) to (4).

Guaiacol thus produced is measured by quantitative or qualitative analysis in the present invention. Examples of quantitative or qualitative analysis of guaiacol includes gas chromatography/mass spectrometry (GC-MS analysis), HPLC, and color reaction. Among these, GC-MS analysis and color reaction are preferable.

In case of measuring by GC-MS analysis, a liquid culture sample, which may produced guaiacol, is served as a sample for GC-MS analysis usually after filtering, for example, through a filter for sterilization (preferably cartridge type filter) having a pore size of 0.2 to 0.8µ to remove bacteria cells, and extracting the filtrate with n-hexane using a solid phase extraction column (for example, Sep-Pak Plus t-C18, manufactured by Waters Co.) connected to a dehydration column (for example, hydro-column, manufactured by Uni Flex Co.). With regard to a general method of GC-MS analysis, see, for example, Lopez, Ricardo et al., Determination of minor and trace volatile compounds in wine by solid-phase extraction and gas chromatography with mass spectrometric detection, Journal of Chromatography, 966 (1-2), 167-177 (2002).

The data obtained by GC-MS analysis can be used for determining the presence or absence of the objective bacteria capable of producing guaiacol (e.g., thermotolerant acidophilic bacteria, bacteria of *Bacillus*) or contamination degree using an indication such as at least 0.05 ppm of guaiacol in orange juice.

In case of measuring guaiacol by the color reaction, a preferable method includes a method of performing a color reaction by an oxidation reaction using peroxidase as a catalyst and detecting the color by spectrophotometry or visual observation.

Specifically, for example, the method is carried out by mixing the filtrate obtained by filtrating the above culture sample, which may contain the produced guaiacol, through a filter for sterilization with an acid buffer solution (or neutral buffer solution), adding hydrogen peroxide water and then peroxidase, mixing them, usually maintaining the mixture under the pH within a range from 3.5 to 6.0 (preferably from 3.5 to 4.5) at a temperature of 15 to 40° C., and preferably at a room temperature (for example, 20 to 30° C.) for 3 to 10 minutes, and preferably 5 to 7 minutes (over 10 minutes is not preferable because of a problem such as discoloring), and detecting the degree or presence or absence of coloring by spectrophotometry using a conventional absorption measuring device, or visual observation. The acid buffer solution includes, for example, phosphate-citrate buffer, phthalate buffer, or tartrate buffer solutions, and the pH is usually within a range from 3.5 to 6.0, and preferably 3.5 to 5.0. The proportion of the buffer solution is usually within a range from 50 to 200% (v/v) based on the sample. The neutral buffer solution includes, for example, potassium phosphate buffer or Sørensen buffer solution, and the pH is usually within a range from 5.0 to 8.0, and preferably 6.5 to 7.5. The proportion of the buffer solution is usually from 50 to 200% (v/v) based on a sample. The amount of hydrogen peroxide water is usually within a range from 1 to 5 mM based on a sample. The amount of the peroxidase is usually within a range from 1 to 20 units (preferably 5 to 10 U) per 3 ml of the sample. The measuring wavelength of the reaction solution is usually within a range from 450 to 500 nm, and preferably 460 to 480 nm.

The results of the measurement of the absorbance or measurement of the color reaction by visual observation can be used for determination of the presence or absence of the objective bacteria capable of producing guaiacol or contamination degree, for example, by previously forming a calibration curve or a standard color table for visual observation, which has a relation with the cell number concentration of the objective bacteria, the amount of guaiacol produced, and the absorbance of the colored solution, using the presence or absence or degree of brown color as an indicator.

In preferable aspect, information with higher reliability can be obtained by measuring both the above-mentioned GC-MS analysis and color reaction.

The present invention also relates to a kit for detection of bacteria capable of producing guaiacol (thermotolerant acidophilic bacteria (particularly bacteria of the genus *A. acidoterrestris*, *Bacillus* (particularly *B. subtilis*), that is a kit comprising a container, and an acid culture medium (or neutral culture medium) containing a vanillic acid substrate for production of guaiacol, which is contained in the container and also sterilized and sealed. The present invention also relates to a detection kit comprising the kit and a means for detection of guaiacol in combination. A basic principle of the detection kit of the present invention lies in the above-mentioned detection method of the present invention.

Figure 5:
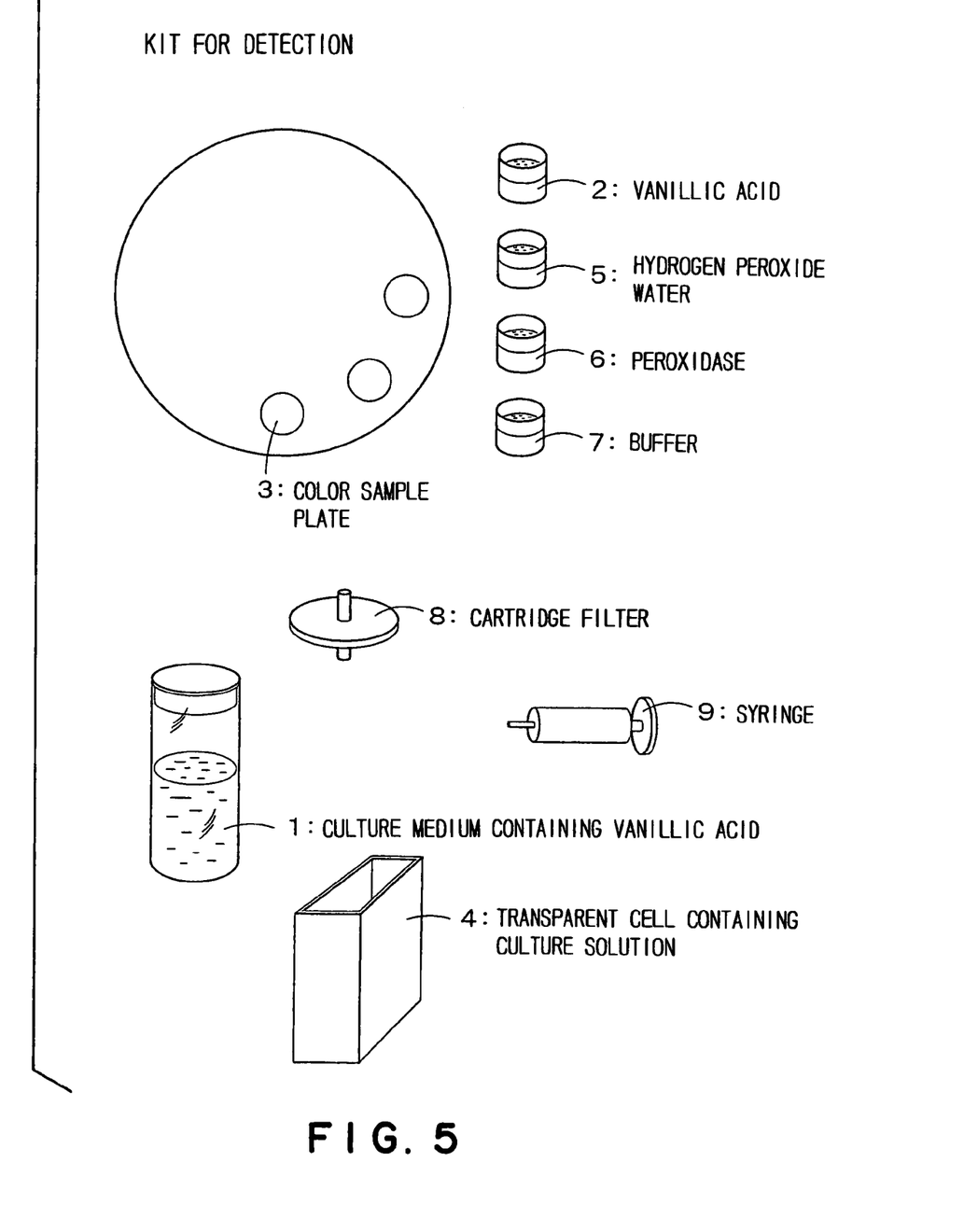
FIG. 5 is an explanatory scheme showing a typical kit for detection of bacteria capable of producing guaiacol according to the present invention.

FIG. 5 shows a preferable example of a kit for detection of bacteria capable of producing guaiacol according to the present invention.

A detection kit (1) is produced by enclosing an acid culture medium (or neutral culture medium) containing vanillic acid added therein in a proper container (made of plastic or glass tube) and subjecting to sterilization (e.g., autoclaving). Examples of the acid culture medium include liquid medium such as YSG medium or BAM medium. Examples of the neutral culture medium include liquid medium such as standard liquid medium or TSB medium. The concentration of vanillic acid is usually within a range from 25 to 200 ppm based on the culture medium. The detection kit (1) can be used for GC-MS analysis when used alone.

The detection kit comprising the detection kit (1) and a means for detection of guaiacol in combination can detect guaiacol without using an equipment for GC-MS analysis or the like. Typical example of the means for detection of guaiacol is based on the color reaction (preferably oxidation reaction of guaiacol using peroxidase as a catalyst). The detection kit comprising the mean in combination with the kit can perform both of GC-MS analysis and color reaction, and determination with higher reliability can be carried out by both measurements.

Preferable embodiment of the detection kit of the present invention based on the color reaction (oxidation reaction by peroxidase) will be described below.

The detection kit shown in FIG. 5 is composed of the kit (1) (vanillic acid-containing medium (1)), a vanillic acid substrate (2), hydrogen peroxide water as a means for detection of guaiacol detection (5), a peroxidase enzyme (6), a buffer solution for enzymatic reaction (7), a filter for filtrating a culture solution (e.g., cartridge filter (8)), a manual pump for filtrating a culture solution (e.g., syringe (9)), a transparent cell containing a culture filtrate (4), and a color sample plate (3).

In the present invention, the detection kit preferably comprises a combination of all components (1) to (9) and may comprises any combination of them, however, the component (1) or (2) and the components (5) to (7) are essential when used. Basically, a combination of the kit (1) and the components (3) to (9) or the elements (2) to (9) enables preferable measurement.

In FIG. 5, the component (1) denotes a sterilized and sealed container containing a vanillic acid-containing acid culture medium. The component (2) is prepared by dissolving a vanillic acid substrate for production of guaiacol in a solvent such as ethanol or water and enclosing the solution in a plastic container or the like. The concentration of vanillic acid is usually within a range from 1 to 10% (w/v). The component (5) is prepared by enclosing hydrogen peroxide water as an oxidizing agent for enzymatic reaction in a plastic container or the like. The component (6) is prepared by dissolving peroxidase as an enzyme for color reaction in water and enclosing the solution in a plastic container or the like. The concentration of peroxidase (titer or specific activity) is usually within a range from 1 to 20 U/3 ml. The component (7) is prepared by enclosing an acid buffer solution (or neutral buffer solution) for enzymatic reaction in a plastic container or the like. The component (8) denotes a cartridge filter for removing particles such as bacterial cells from a sample culture solution before an enzymatic reaction by filtration. The component (9) denotes a syringe made of plastic or the like, which is provided with a cartridge filter, thereby to suck up the sample culture solution and filter particles such as bacterial cells to obtain the filtrate. The component (4) denotes a transparent cell (made of glass or the like) for containing a culture solution, in which the filtrate obtained in (9) is poured and subjected to the peroxidase enzyme reaction, and then to visual observation or absorbance measurement. The component (3) is a color sample plate prepared based on a relation between coloring in the enzymatic reaction and the amount of guaiacol produced, which represents the level of coloring (brown color) according to the concentration of guaiacol.

An examples of a basic aspect of the method for detecting bacteria capable of producing guaiacol (e.g., thermotolerant acidophilic bacteria, and bacteria of the genus *Bacillus*) using the detection kit of the present invention is as follows. The conditions such as amount and concentration of the reagent in the respective kits, and amount of each reagent and specimen can be optionally set according to the above-mentioned method of the present invention. The conditions such as culture, enzymatic reaction and measurement are basically the same as those in this detection method of the present invention.

1) A specimen such as acidic beverage (or neutral beverage) is added and dispersed in a vanillic acid-containing culture medium (1) and cultured for a fixed time (usually 18 to 48 hours at a temperature of 45 to 50° C.) with shaking to obtain a filtrate using (8) and (9) and then the filtrate is subjected to GC-MS analysis, or guaiacol is measured by using the components (3) to (7) of the kit.
2) Vanillic acid (2) is added and dispersed in a specimen such as acidic beverage (or neutral beverage) and cultured for a fixed time (usually 18 to 48 hours at a temperature of 45 to 50° C.) with shaking to obtain a filtrate using (8) and (9) and then the filtrate is subjected to GC-MS analysis, or guaiacol is measured by using the components (3) to (7) of the kit.
3) A liquid culture or colony obtained previously by selective culture (pre-culture) is added and dispersed directly in a vanillic acid containing culture medium (1), or added and dispersed optionally after diluting with sterilized water, a proper buffer solution (for example, potassium phthalate buffer solution (particularly, for acidic beverage), potassium phosphate buffer solution (particularly, for a neutral beverage), a liquid culture medium (for example, YSG medium (particularly, for acidic beverage), a TSB medium (particularly, for a neutral beverage) or the like, and cultured for a fixed time (usually 0.5 to 8 hours at a temperature of 45 to 50° C.) with shaking to obtain a filtrate using (8) and (9), and then the filtrate is subjected to GC-MS analysis, or guaiacol is measured by using the components (3) to (7) of the kit. 4) Vanillic acid (2) is added and dispersed in a liquid culture obtained previously by selective culture (pre-culture), the dilution of the culture or colony, cultured for a fixed time (usually 0.5 to 1.5 hours at a temperature of 45 to 50° C.) with shaking to obtain a filtrate using (8) and (9), and then the filtrate is subjected to GC-MS analysis, or guaiacol is measured by using the components (3) to (7) of the kit.

The present invention also relates to a method for rapid determination of proliferation properties of bacteria capable of producing guaiacol in food and beverage, which comprises incubating a sporophyte of spore-forming bacteria capable of producing guaiacol for a fixed time in the food and beverage in the presence of vanillic acid, and measuring the produced guaiacol by qualitative or quantitative analysis.

According to the determination method of the present invention, spores of spore-forming bacteria capable of producing guaiacol are used as an indicator bacterium and the spore cells are incubated in food and beverage (particularly beverage), and then the produced guaiacol is measured, thereby determining proliferation properties of the bacterial cells in food and beverage (that is, acidic beverage (fruit juice, vegetable juice, or sport drink), neutral food and beverage (dairy product (semi-product yogurt, milk, or fresh milk), rice gruel, tea, or mixed tea) as actual products.

As the indicator bacterium used in this determination method, bacteria of the genus *Alicyclobacillus* (for example, *A. acidoterrestris* and *A. acidiphilus*) and bacteria of the genus *Bacillus* (for example, *B. subtilis* and *B. megaterium*) and the like can be used. Among these bacteria, *A. acidoterrestris* is typical. Preferable embodiment of the determination method of the present invention in a combination of the indicator bacterium and food and beverage includes determination for proliferation properties of *A. acidoterrestris* (spores) in sport drink and determination for proliferation properties of *Bacillus subtilis* (spores) in tea or mixed tea.

The amount of vanillic acid to be added in food and beverage is usually within a range from about 25 to 200 ppm, and preferably from about 50 to 100 ppm, based on the food and beverage (corresponding to a culture medium (acid or neutral culture medium) in the detection method), similar to the case of the above-mentioned detection method and detection kit. In the determination method, the conditions and procedures such as culture including the addition of vanillic acid and use of an acid or neutral culture medium as well as measurement of guaiacol itself are basically the same as those in case of the above-mentioned determination method and detection kit of the present invention. Therefore, the incubation in the determination method and the measurement of the produced guaiacol by qualitative or quantitative analysis can be carried out according to the determination method and detection kit of the present invention. When using the detection kit, a vanillic acid-containing medium (1) is not required if vanillic acid (2) is used.

In the determination method, the concentration of bacterial cells in a culture solution (food and beverage) containing vanillic acid added therein is the same as that in case of using a liquid culture or colony as a specimen in the determination method and detection kit of the present invention. The concentration is preferably controlled within a range from about $10^5$ to $10^7$/ml, and more preferably from about $10^5$ to $10^6$/ml.

The present inventors have found that the bacteria capable of producing guaiacol used in the determination method of the present invention are spore-forming bacteria and guaiacol is not produced from a spore, but produced if budding of spores occurs, and based on this finding, that the determination method makes it possible to determine that guaiacol is produced (that is, proliferation properties exist) if budding of spores occurs when using sporophytes. Therefore, according to the data obtained by the measurement of guaiacol (e.g., GC-MS analysis, HPLC, color reaction), for example, proliferation properties of bacteria capable of the objective producing guaiacol (e.g., thermotolerant acidophilic bacteria, and bacteria of the genus *Bacillus*) is determined to be positive by using an indicator such as 0.05 ppm of guaiacol in orange juice. As described above, proliferation properties of the objective bacteria capable of producing guaiacol can be determined by the color reaction using a standard color table for visual observation (see, for example, detection kit in FIG. 5). In preferable aspect, determination with higher reliability can be carried out by measuring both GC-MS analysis and color reaction. In case it is determined to have proliferation properties by the measurement of guaiacol, it is useful for example to study of sterilization conditions of food and beverage and control of raw materials of food and beverage.

A conventional determination method (see aforementioned "Background Art") required at least two weeks, while the determination method of the present invention as mentioned above makes it possible to determine the presence or absence of proliferation properties within only about 2 days, as shown in Example 9 described hereinafter, in case of inoculating high concentration (for example $10^5$/ml) of spores.

As described above, the present invention can provide a method for rapid determination of proliferation properties of bacteria capable of producing guaiacol.

The detection method, the detection kit and the method for rapid determination of proliferation properties of bacteria capable of producing guaiacol according to the present invention will be described in more detail in the following examples.

EXAMPLES

The following examples further illustrate the present invention in detail, but the present invention is not limited to thereto.

In the present specification, the indication % is by weight unless otherwise specified.

Example 1

Pre-culture: Test bacterium *Alicyclobacillus acidoterrestris* TA-27 (KBL304) was pre-cultured under the following conditions. Culture medium: liquid YSG medium; shake culture at 45° C. for 17 hours; inoculated bacteria number: $10^4$/ml.

Comparison in a guaiacol production rate between the addition of vanillin and the addition of vanillic acid:

(1) To a test bacteria pre-culture solution (logarithm growth phase), vanillin or vanillic acid was added to a final concentration of 100 ppm. Shake culture was carried out at 45° C. (for 15 minutes, 30 minutes . . . ). As a blank, an uninoculated liquid YSG medium was prepared and vanillin or vanillic acid was added to a final concentration of 100 ppm in the same manner as in case of the sample.

(2) 2 ml of the filtrate obtained by filter-sterilization of the sample (1) was transferred in a test tube and 1 ml of 100 mM potassium phthalate buffer solution (pH 4.5) was added, followed by mixing. Subsequently, 8.5 µl of 3% of hydrogen peroxide water was added, followed by mixing. Finally, 3.0 µl of peroxidase* was added and, after mixing, the mixture was allowed to stand at a room temperature for 10 minutes and the absorbance at 470 nm was measured. (*Peroxidase: A solution prepared by diluting Peroxidase for Horseradish (WAKO) with 15 mM sodium phosphate buffer solution to 1.62 U/µl). The results of a comparison test in a guaiacol production rate between the addition of vanillin and the addition of vanillic acid are shown in Tables 1 and 2, and FIG. 1.

TABLE 1

| | In case of addition of vanillin | |
|---|---|---|
| Shaking time | OD$_{470}$ | Guaiacol concentration (ppm) |
| 15 minutes | 0 | — |
| 30 minutes | 0 | — |
| 45 minutes | 0 | — |
| 1 hour | 0 | — |
| 2 hours | 0.1017 | 3.5 |
| 3 hours | 0.2324 | 7.9 |

TABLE 2

| | In case of addition of vanillic acid | |
|---|---|---|
| Shaking time | OD$_{470}$ | Guaiacol concentration (ppm) |
| 15 minutes | 0 | — |
| 30 minutes | 0 | — |
| 45 minutes | 0.0835 | 2.9 |
| 1 hour | 1.3097 | 45.2 |

Figure 1:
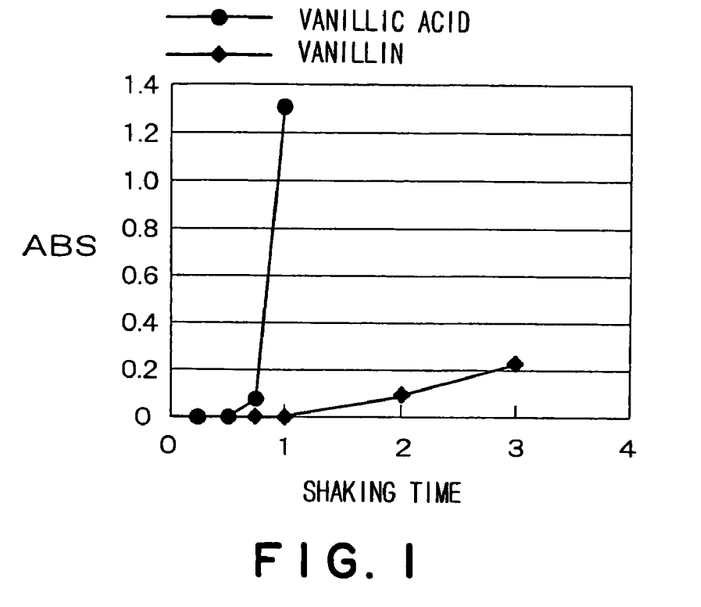
FIG. 1 is a graph showing the results of comparison in a guaiacol production rate between the case of the addition of vanillic acid and the case of the addition of vanillin in Example 1.

As is apparent from Tables 1 and 2, and FIG. 1, in case of the addition of vanillic acid, the guaiacol production rate of *Alicyclobacillus acidoterrestris* TA-27 (KBL304) is by far higher than that in case of the addition of vanillin. Therefore, it has been found that after pre-culture, in case of the addition of vanillin, the detection of bacteria requires about 2 to 3 hours as a detection limit, while the evaluation can be performed even by visual observation within one hour in case of the addition of vanillic acid.

Example 2

In the same manner as in Example 1, except that a test bacteria pre-culture solution in a stationary phase was used and a potassium phosphate buffer solution (pH 6.8) was used as a buffer solution for peroxidase reaction, a comparison in a guaiacol production rate of *Alicyclobacillus acidoterrestris* TA-27 (KBL304) between the addition of vanillin and the addition of vanillic acid was made. The results are shown in Tables 3 and 4, and FIG. 2.

TABLE 3

| | In case of addition of vanillin | |
|---|---|---|
| Shaking time | OD$_{470}$ | Guaiacol concentration (ppm) |
| 30 minutes | 0.0125 | — |
| 1 hour | 0.0344 | — |
| 3 hours | 0.1644 | 10.0 |
| 7 hours | 0.5651 | 33.7 |

TABLE 4

In case of addition of vanillic acid

| Shaking time | OD$_{470}$ | Guaiacol concentration (ppm) |
|---|---|---|
| 30 minutes | 0 | — |
| 1 hour | 0.0008 | — |
| 3 hours | 1.7204 | 102.0 |
| 7 hours | 1.8570 | 110.1 |

Figure 2:
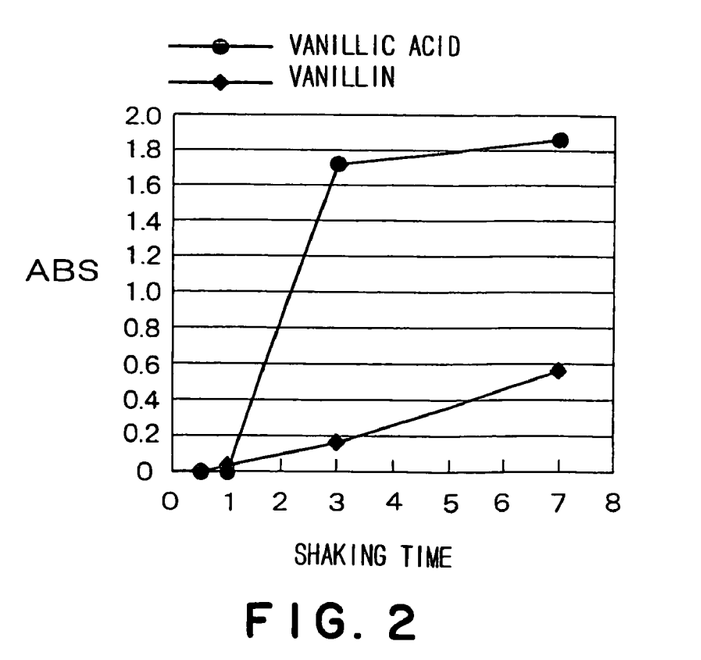
FIG. 2 is a graph showing the results of comparison in a guaiacol-producing rate between the case of the addition of vanillic acid and the case of the addition of vanillin in Example 2.

As is apparent from Tables 3 and 4, and FIG. 2, in case of the addition of vanillic acid, the quaiacol production rate of *Alicyclobacillus acidoterrestris* TA-27 (KBL304) is by far higher than that in case of the addition of vanillin. Therefore, it has been found that after pre-culture, in case of the addition of vanillin, the detection of bacteria requires about 3 to 7 hours as a detection limit, while sufficient evaluation can be performed within 1.5 hours in case of the addition of vanillic acid. As is apparent from the results of Examples 1 and 2, when the specimen is fruit juice beverage or acidic beverage, pre-culture is preferably performed for about one day. When the specimen is a fresh bacterial cell (culture solution in case of a liquid culture medium, colony in case of a solid culture medium), no pre-culture is required.

Example 3

Study of Optimal pH of Peroxidase Reaction

The optimal pH in the peroxidase reaction described in Example 1 (2) was studied. The results are shown in Table 5.

TABLE 5

Results of absorbance as measured when reacted with guaiacol (5 ppm) solution

| PH | OD$_{470}$ |
|---|---|
| 6.8 | 0.0566 |
| 6.0 | 0.0582 |
| 5.0 | 0.0772 |
| 4.5 | 0.0825 |
| 3.5 | 0.0868 |

As is apparent from Table 5, best coloring is achieved at the pH within a range from 4.5 to 3.5 and the optimal pH is within a range from 4.5 to 3.5.

Example 4

Formation of Calibration Curve

Figure 3:
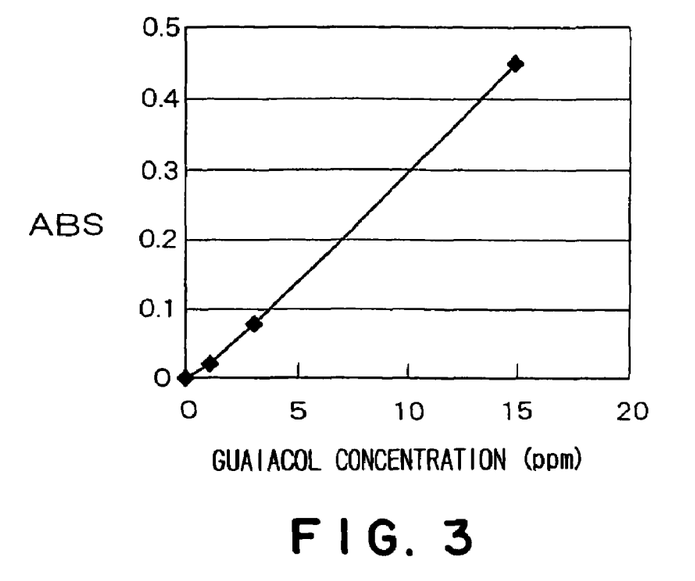
FIG. 3 is a graph showing the measurement results of the guaiacol concentration and $OD_{470}$ using a potassium phthalate buffer solution (pH 4.5).

Using a potassium phthalate buffer solution (pH 4.5) used in Example 3, a calibration curve for the measurement of the guaiacol concentration and ABS (OD470) was formed. The results are shown in Table 6 and FIG. 3.

TABLE 6

Guaiacol concentration and OD$_{470}$ when using potassium phthalate buffer solution (pH 4.5)

| Guaiacol concentration (ppm) | OD$_{470}$ |
|---|---|
| 0 | 0.0000 |
| 1 | 0.0246 |
| 3 | 0.0819 |
| 15 | 0.4457 |

Example 5

Construction of Calibration Curve

Figure 4:
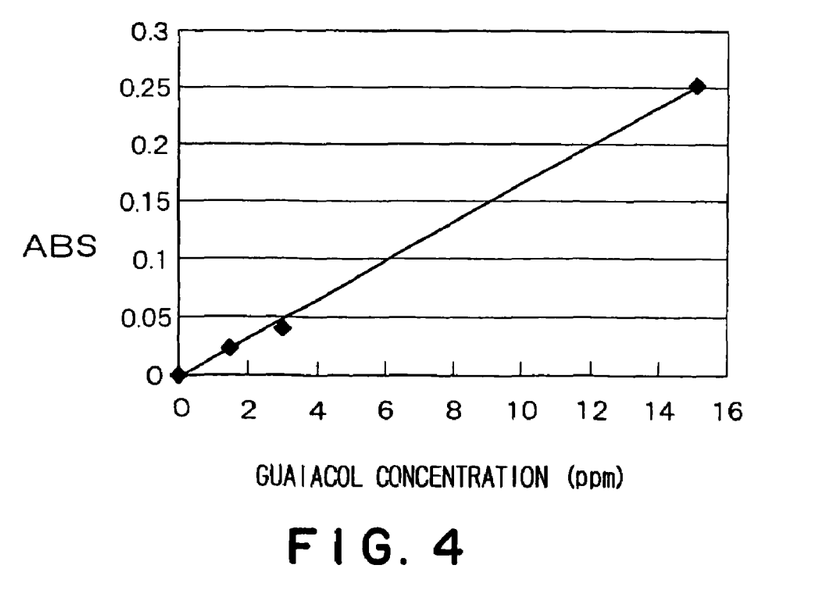
FIG. 4 is a graph showing the measurement results of the guaiacol concentration and $OD_{470}$ using a sodium phosphate buffer solution (pH 6.8).

Using sodium phosphate buffer solution (pH 6.8) used in Example 3, a calibration curve for the measurement of the guaiacol concentration and ABS (OD470) was formed. The results are shown in Table 7 and FIG. 4.

TABLE 7

Guaiacol concentration and OD$_{470}$ when using sodium phosphate buffer solution (pH 6.8)

| Guaiacol concentration (ppm) | OD$_{470}$ |
|---|---|
| 0 | 0 |
| 1.51 | 0.0239 |
| 3.02 | 0.0397 |
| 15.1 | 0.2523 |

As is apparent from Examples 4 and 5, a calibration curve can be formed between the guaiacol concentration and OD470 at pH 4.5, even at pH 6.8.

Example 6

A comparison in effect on selectivity with respect to the detection of the bacteria of the genus *Alicyclobacillus* producing no guaiacol between vanillin and vanillic acid was made. Test bacteria: *Alicyclobacillus acidocaldarius* TA-47 (KBL336). Pre-culture condition: liquid YSG medium, shake culture at 45° C. for 17 hours. *Potassium phthalate buffer solution (pH 5.0) was used.

TABLE 8

In case of addition of vanillin

| Shaking time | OD$_{470}$ | Guaiacol odor |
|---|---|---|
| 7 hours | 0.0612 | — |
| 24 hours | 0.0889 | — |

TABLE 9

In case of addition of vanillic acid

| Shaking time | OD$_{470}$ | Guaiacol odor |
|---|---|---|
| 7 hours | 0 | — |
| 24 hours | 0 | — |

As is apparent from Tables 8 and 9, it was suggested that vanillic acid has high selectivity with respect to the detection of bacteria of the genus *Alicyclobacillus* producing no guaiacol.

Although various dairy products with vanilla flavor are commercially available, the production of a nasty smell component, guaiacol, associated with proliferation of specific *Bacillus* may cause deterioration of flavor, if the conditions are satisfied. The following example is an example wherein a trial of rapidly detecting bacteria, which are isolated from the atmosphere of a dairy product manufacturing factory and are the causative bacteria, was made.

Example 7

(1) Rapid determination of *Bacillus subtilis* Colony by Peroxidase Method

Detection Condition:

To YSG medium of pH 7 with 100 ppm of vanillic acid added thereto, one scrape of a platinum loop of bacterial cells were added. The mixture was cultured at 35° C. (45° C.) with or without shaking and the measurement was carried out by the Peroxidase method (in the same manner as described above).

TABLE 10

| Culture time | Reaction solution pH (YSG) | | | |
|---|---|---|---|---|
| | 3.7 | 4.5 | 5.5 | 7.0 |
| Culture at 35° C. | | | | |
| *B. subtilis* VY-1 ABS (OD$_{470}$) | | | | |
| 1 hour | −0.0104 | −0.0185 | 0.0078 | 0.0083 |
| 2.5 hours | −0.0133 | −0.0039 | −0.0021 | (0.1573) |
| 24 hours | −0.0026 | −0.0156 | (1.6913) | — |
| *B. subtilis* VY-4 ABS (OD$_{470}$) | | | | |
| 1 hour | −0.0142 | −0.0108 | 0.0252 | 0.0519 |
| 2.5 hours | −0.0189 | 0.0030 | (0.1313) | (0.3708) |
| 24 hours | 0.0048 | 0.0249 | — | — |
| Culture at 45° C. | | | | |
| *B. subtilis* VY-3 ABS (OD$_{470}$) | | | | |
| 1 hour | −0.0039 | 0.0090 | 0.0335 | (1.0113) |
| 2.5 hours | −0.0150 | 0.0102 | (0.3639) | — |
| 24 hours | −0.0132 | −0.0087 | — | — |

(Numerical value): Guaiacol production

As is apparent from Table 10, it was confirmed that *B. subtilis* can be also be rapidly detected.

Example 8

(2) Examples of Detection of *Bacillus* Capable of Producing Guaiacol

Using several strains of *B. subtilis* and *B. megaterium* which have been reported to produce guaiacol in publications and each one of typical strains among other *Bacillus* wherein the presence or absence of the production of guaiacol is previously made clear, it was confirmed whether or not the detection can be carried out by the method (1).

TABLE 11

| | Culture time (hours) | |
|---|---|---|
| Symbol | 4 | 72 |
| *B. subtilis* ABS (OD$_{470}$) | | |
| KBL15 | (1.4808) | — |
| IFO3134 | (0.5430) | — |
| KBLIFO13719 | (1.3289) | — |
| KBL159 | −0.0314 | (0.8180) |

TABLE 11-continued

| | Culture time (hours) | |
|---|---|---|
| Symbol | 4 | 72 |
| ATCC6633 | (0.7799) | — |
| KBL379 | 0.0251 | (1.0694) |
| KBL382 | −0.0384 | (0.6505) |
| KBL397 | (0.7429) | — |
| KBL347 | (1.3915) | — |
| *B. megaterium* ABS (OD$_{470}$) | | |
| KBL155 | (1.2063) | — |
| KBL156 | (1.2101) | — |
| KBL157 | (1.0389) | — |
| KBL158 | (1.1441) | — |
| KBL381 | (0.9443) | — |
| KBL383 | (1.1105) | — |

TABLE 12

| | Other ABS (OD$_{470}$) | |
|---|---|---|
| | Culture time (hours) | |
| Symbol | 4 | 72 |
| *B. coagulans* JCM2257* | 0.0004 | −0.0248 |
| *B. polymyxa* KBL274 | (0.8016) | — |
| *B. sphaericus* 303* | 0.0046 | 0.0083 |
| *B. licheniformis* IFO12195 | (0.9201) | — |
| *B. circulans* KBL166* | 0.0168 | −0.0201 |

*Strain producing no guaiacol
(Numerical value): Guaiacol production (Results)

As is apparent from Tables 10 to 12, almost all of strains of *B. subtilis* and *B. megaterium* exhibited the positive reaction. In other *Bacillus*, all bacteria capable of producing guaiacol were positive and this method was effective as a method for detecting harmful bacteria.

Example 9

Test method

Using *A. acidoterrestris*-proliferative acid sport drink (comprising 1% fruit juice, 0.18% citric acid, 9% isomerized sugar and 0.25% flavor) containing 100 ppm of vanillic acid added therein, two steps of preparations containing $10^3$ and $10^5$ spores/ml of *A. acidoterrestris* spores were prepared therein and cultured at 45° C. with shaking. As a control, a sample prepared by adding 300 ppm of sodium benzoate having the effect of inhibiting the growth of the same bacteria to the same solution was used. The resulting solution was sampled with a lapse of time and the amount of guaiacol produced was measured by the Peroxidase method.

Conditions
  Test bacteria: *Alicyclobacillus acidoterrestris* KBL304
    (pre-culture: stored at room temperature after culturing YSG at 45° C. for 7 days)
  Inoculate: $10^3$ spores/ml, $10^5$ spores/ml
  Reaction solution:
  (1) Positive control: acidic sport drink
  (2) Negative control: acidis sport drink+300 ppm of sodium benzoate
  Both controls wherein 100 ppm of vanillic acid was added
  Incubation: shaken at 45° C. for a few days
  Positive: proliferative
  Negative: non-proliferative

TABLE 13

| Culture time | ABS (OD$_{470}$) | |
| --- | --- | --- |
| | Positive | Negative |
| Cell number of inoculum: 10$^3$ spores/ml | | |
| 48 hours | 0.0291 | 0.0021 |
| 72 hours | 0.0260 | 0.0024 |
| Cell number of inoculum: 10$^5$ spores/ml | | |
| 48 hours | (0.7809) | −0.0043 |
| 72 hours | — | −0.0053 |

(value): Guaiacol production (Results)

As is apparent from Table 13, a conventional method required two weeks for determination, while this method made it possible to perform a determination within 2 days in case of inoculating spores in high concentration of 10$^5$/ml.

Example 10

Detection Kit

As shown in FIG. 5, the detection operation is further simplified when using a detection kit comprising all or any combination of (1) an acid culture medium containing vanillic acid, which is contained in a sealed container and sterilized, (2) vanillic acid, (3) a color sample plate, (4) a transparent cell containing a culture filtrate (4 to 5 ml by volume), (5) hydrogen peroxide water, (6) peroxidase, (7) a buffer solution, (8) a cartridge filter for filtration of a culture solution (preferably 0.4μ), and (9) a syringe for filtration of a culture solution. That is, it is a kit which can detect thermotolerant acidophilic bacteria capable of producing guaiacol, particularly *A. acidoterrestris* only by using a color sample plate and a cell containing a culture filtrate without using an expensive equipment.

Specifically, using the method as described in Example 1, a specimen such as fruit juice or acidic beverage, which may be contaminated with thermotolerant acidophilic bacteria, is inoculated into (1), flowed by shake pre-culture at 45° C. for about one day, or 100 ppm of vanillic acid (2) is directly added to the specimen, followed by shake culture at 45° C. for about one day. About 2 ml of this sample is sterilized by filtration using (8) and (9) and put in a container (4), and then 1 ml of a buffer solution (7) (100 mM potassium phthalate buffer solution, pH 4.5) is added, followed by mixing. Subsequently, 8.5 μl of 3% hydrogen peroxide water (5) is added, followed by mixing. Finally, 3.0 μl (titer: 5 units) of peroxidase (6) is added, after mixing and maintaining at room temperature for 10 minutes, color tone was compared using (3), thereby to detect and verify thermotolerant acidophilic bacteria capable of producing guaiacol, particularly *A. acidoterrestris*.

A specimen such as a culture solution cultured in a liquid culture medium, or a colony cultured in a solid culture medium, or acidic beverage such as fruit juice containing proliferated thermotolerant acidophilic bacteria is appropriately diluted, e.g., with sterilized water, a buffer solution, a culture medium or the like and inoculated into (1). Alternatively, 100 ppm of vanillic acid (2) is directly added to the above dilute solution, followed by shake culture for about one hour. About 2 ml of this sample is sterilized by filtration using (8) and (9), and then put in a container (4). 1 ml of a buffer solution (7) (100 mM potassium phthalate buffer solution, pH 4.5) is added, followed by mixing. Subsequently, 8.5 μl of 3% hydrogen peroxide water (5) is added, followed by mixing. Finally, 3.0 μl (titer: 5 units) of peroxidase (6) is added and, after mixing and maintaining at a room temperature for 10 minutes, color tone was compared with (3), thereby to detect and verify thermotolerant acidophilic bacteria capable of producing guaiacol, particularly *A. acidoterrestris*. This corresponds to the practical conditions of Example 1.

INDUSTRIAL APPLICABILITY

According to the present invention as described above, the following advantages can be obtained.

The present invention can provide a method for detecting bacteria capable of producing guaiacol (typically, thermotolerant acidophilic bacteria (particularly, *A. acidoterrestris*) and bacteria belonging to the genus *Bacillus* (particularly, *B. subtilis*) even more rapidly with higher sensitivity as compared with the case of using vanillin by culturing or incubating a culture solution containing a specimen for a predetermined time in the presence of vanillic acid, and measuring the produced guaiacol by qualitative or quantitative analysis.

The present invention can provide a simple method for detecting bacteria capable of producing guaiacol, wherein the produced guaiacol is measured by GC-MS analysis or color reaction.

The present invention can provide a simple method for detecting bacteria capable of producing guaiacol, wherein the color reaction with guaiacol uses peroxidase and is detected by spectrophotometry or visual observation.

The present invention can provide a more rapid and simple kit for detection of bacteria capable of producing guaiacol by using a combination of vanillic acid and a color reaction reagent.

The present invention can perform determination with higher reliability by measuring both of the above-mentioned GC-MS analysis and color reaction.

The present invention can provide a method for rapid determination of proliferation properties of bacteria cells in actual food and beverage using spores of bacteria capable of producing guaiacol as an indicator bacterium.

The invention claimed is:

1. A method for rapidly detecting the presence of bacteria which produce guaiacol, comprising the steps of:
   preparing a liquid culture or colony as a specimen by selective culture or pre-culture;
   adding the liquid culture or colony, directly or after optionally diluted, to a liquid medium containing vanillic acid to form a second liquid medium;
   culturing or incubating the second liquid medium; and
   measuring the presence of guaiacol by a color change in the cultured or incubated second liquid medium employing an oxidation reaction by adding to the cultured or incubated second liquid medium a peroxidase catalyst.

2. The method of claim 1, wherein the bacteria which produce guaiacol to be detected are thermotolerant acidophilic bacteria and are cultured or incubated under acidic conditions with a pH within a range of from 3.0 to 5.0.

3. The method claim 1, wherein the bacteria which produce guaiacol to be detected are bacteria belonging to the genus *Bacillus* and are cultured or incubated under a pH within a range of from 5.5 to 7.5.

4. The method claim 2, wherein the thermotolerant acidophilic bacteria is *Alicyclobacillus acidoterrestris*.

5. A kit for rapid detection of bacteria which produce guaiacol comprising:

a medium containing vanillic acid as a substrate, which is to be added to a liquid culture or colony as a specimen which has been obtained by selective culture or preculture;

a combination of hydrogen peroxide solution, a peroxidase enzyme and a buffer for enzymatic reaction to detect guaiacol;

wherein the medium and the combination are contained in sterilized and sealed containers.

6. The kit of claim 5, wherein the bacteria which produce guaiacol to be detected are thermotolerant acidophilic bacteria and an acidic culture medium having a pH within a range of from 3.0 to 5.0 is contained in the kit.

7. The kit of claim 5, wherein the bacteria which produce guaiacol to be detected are bacteria belonging to the genus *Bacillus* and a culture medium having a pH within a range of from 5.5 to 7.5 is contained in the kit.

8. The kit of claim 6, wherein the thermotolerant acidophilic bacteria is *Alicyclobacillus acidoterrestris*.

9. A method for rapid determination of proliferation properties of bacteria which produce guaiacol in food and beverage comprising the steps of:

preparing a sporophyte of spore-forming bacteria capable of producing guaiacol by selective culture or preculture;

adding the sporophyte of spore-forming bacteria, directly or after optionally diluted, to a food or beverage in the presence of vanillic acid;

incubating the sporophyte; and measuring the presence of guaiacol by a color change after incubation by employing an oxidation reaction by adding to the incubated sporophyte a peroxidase catalyst.

10. The method of claim 9, wherein the spore-forming bacteria which produce guaiacol are thermotolerant acidophilic bacteria.

11. The method of claim 10, wherein the thermotolerant acidophilic bacteria is *Alicyclobacillus acidoterrestris*.

* * * * *